United States Patent [19]
Yagi et al.

[11] Patent Number: 5,439,827
[45] Date of Patent: Aug. 8, 1995

[54] COMPOSITION FOR DETECTING PEROXIDE ACTIVE MATERIAL

[75] Inventors: Yuji Yagi; Tamaki Kagawa; Hiroshi Tamura; Tetsuya Ota, all of Kyoto, Japan

[73] Assignee: Kyoto Daiichi Kagaku Co., Ltd., Kyoto, Japan

[21] Appl. No.: 148,321

[22] Filed: Nov. 8, 1993

[30] Foreign Application Priority Data

Nov. 9, 1992 [JP] Japan ................................. 4-298514

[51] Int. Cl.$^6$ ...................... G01N 33/72; G01N 21/75
[52] U.S. Cl. .......................................... 436/66; 422/56; 422/57; 436/95; 436/166; 436/175
[58] Field of Search ...................... 422/56, 57; 436/66, 436/95, 166, 175

[56] References Cited

U.S. PATENT DOCUMENTS

| | | | |
|---|---|---|---|
| 3,012,976 | 12/1961 | Adams et al. | 436/66 |
| 3,504,004 | 3/1970 | Roos | 556/148 |
| 4,295,853 | 10/1981 | Kasahara et al. | 436/66 |
| 4,303,409 | 12/1981 | Ogawa et al. | 436/93 |
| 4,310,626 | 1/1982 | Burkhardt et al. | 436/66 X |
| 4,587,220 | 5/1986 | Mayambala-Mwanika et al. | 436/66 |
| 4,743,559 | 5/1988 | Koevér et al. | 436/66 X |
| 4,755,472 | 7/1988 | Ismail et al. | 436/66 |
| 4,954,451 | 9/1990 | Albarella et al. | 436/66 X |
| 5,196,167 | 3/1993 | Guadagno et al. | 422/56 |

FOREIGN PATENT DOCUMENTS

| | | |
|---|---|---|
| 0027236 | 4/1981 | European Pat. Off. . |
| 0037056 | 10/1981 | European Pat. Off. . |
| 0043469 | 1/1982 | European Pat. Off. . |
| 0123115 | 10/1984 | European Pat. Off. . |
| 0392305 | 10/1990 | European Pat. Off. . |
| 2455283 | 11/1980 | France . |
| 43-51959 | 12/1992 | Japan ................ 436/66 |

OTHER PUBLICATIONS

Inorganica Chimica Acta, B. Bansch et al., The Oxidation of L–Ascorbic Acid . . . , vol. 201, pp. 75–82, (1992).
R. Sunaga et al. *Igaku to Yakugaky*, 1992, 28, 1267–1275.
P. Martinez et al. *Inorg. Chim. Acta* 1987, 136, 11–16.
R. Sunaga et al. *Chem. Abstr.* 1993, 119, 265852m.

*Primary Examiner*—James C. Housel
*Assistant Examiner*—Arlen Soderquist
*Attorney, Agent, or Firm*—Birch, Stewart, Kolasch & Birch

[57] ABSTRACT

A composition for detecting or quantitatively measuring a peroxide active material in a sample, containing an organic hydroperoxide, a chromogen, and an iron (III) complex of the formula: $[(OOC-X-COO)_3Fe]M_3$ in which X is an alkylene group:$-(CH_2)_n-$ ($n = 0 - 5$) or an allyl group, and M is a monovalent cation, which can eliminate the influence of reducing compounds such as ascorbic acid contained in the sample.

7 Claims, No Drawings

COMPOSITION FOR DETECTING PEROXIDE ACTIVE MATERIAL

BACKGROUND OF THE INVENTION

1. Field of the Invention

The present invention relates to a composition for detecting or quantitatively measuring a peroxide active material in a sample. More particularly, the present invention relates to a composition for detecting or quantitatively measuring a peroxide active material which can eliminate an influence of a reducing compound such as ascorbic acid and the like contained in the sample.

2. Description of the Prior Art

When a peroxide active material in a sample is detected or quantitatively measured, ascorbic acid contained in the sample will have several adverse affects on the measurement of the peroxide active material, since it acts as a strong reducing agent. To avoid the influence of the reducing compound such as ascorbic acid, various techniques using a metal ion as an oxidizing agent have been developed.

(1) J. Am. Chem. Soc., 89, 4176 (1967); 89, 7104 (1967); and 90, :3:386 (1968) describe dynamic study of oxidation of ascorbic acid according to pH values in the presence of iron and copper chelates, and revealed that the metal ion oxidized ascorbic acid. However, these papers do not relate to the study of behavior of ascorbic acid in an assay system.

(2) Japanese Patent Publication No. :39871/1988 (corresponding to U.S. Pat. No. 4,288,541 and EP-A-0 027 2:36) discloses the addition of mercury (II) sarcosinate to a composition for analysis to avoid the adverse influence of a salt of ascorbic acid. However, when such metal complex is added to a composition for analysis containing an organic hydroperoxide and an indicator, the indicator reacts with the metal complex to provide a false-positive result. In addition, the mercury complex is not preferable because of toxicity of mercury.

(3) Japanese Patent Publication No. 67139/1988 (corresponding to EP-A-0 043 469) discloses a Co (III) complex as a compound which removes an interfering function of ascorbic acid. However, when the Co (III) complex is added to the composition for analysis containing the organic hydroperoxide and the indicator, the indicator reacts with the metal complex to provide a false-positive result.

(4) Japanese Patent Kokai Publication No. 286099/1990 (corresponding to U.S. Pat. No. 5,079,140 and EP-A-O 392 305) discloses a system containing a first oxidizing agent comprising a water-soluble polymer which generates a copper (II) complex and a second oxidizing agent selected from the group consisting of inorganic oxidizing compounds, organic peroxides and organic N-haloderivative. However, the oxidizing rate of the copper (II) complex is low, and this system is not effective.

(5) Japanese Patent Publication No. 4123/1989 discloses the addition of a divalent or trivalent iron complex of a compound of the formula: $R_1R_2NCH_2COOH$ or $R_3R_4NXNR_5CH_2COOH$ or a divalent or trivalent iron complex of gluconic acid to remove ascorbic acid in the measurement of components in body fluids.

(6) Japanese Patent Publication No. 18630/1992 (corresponding to U.S. Pat. No. 4,587,220 and EP-A-0 123 115) discloses the addition of a trivalent iron chelate of a polycarboxyalkylamine derivative to a composition for detecting the peroxide active material.

(7) In addition, Canada Patent No. 844,564 discloses a testing piece comprising a porous part impregnated with a glucose-responsive reagent, and an additional part which receives a urine sample and contains an ion-exchange material that can absorb ascorbic acid in the urine. The testing piece carrying the iron-exchange material has a complicated structure and requires a longer time for analysis than a conventional assay methods.

(8) Japanese Patent No. 39198/1981 and U.S. Pat. No. 4,168,205 eliminate the influence of ascorbic acid by the addition of ascorbic acid oxidase to a formulation in a test reagent paper. While this method is effective, it is uneconomical since a large amount of ascorbic acid oxidase is necessary to eliminate the interference of ascorbic acid. In addition, ascorbic acid oxidase reacts with ascorbic acid but does not with other reducing materials, and is a very unstable enzyme.

(9) Japanese Patent Publication No. 4861/1990 (corresponding to U.S. Pat. No. 4,743,559 and EP-A-0 037 056) discloses the addition of an iodate (pH of 5 to 9) in an amount of 0.5 to 2 g/dl to a test reagent to eliminate the influence of the reducing material such as ascorbic acid.

(10) Japanese Patent Publication No. 15280/1989 discloses the treatment of a sample with iodic acid or iodate to eliminate the influence of the reducing material. However, iodine which is liberated by the reaction of the reducing agent with the iodic acid or iodate oxidizes various indicators to provide false-positive result. Further, the iodate oxidizes the indicator to color the background.

SUMMARY OF THE INVENTION

One object of the present invention is to provide a novel composition for detecting or quantitatively measuring a peroxide active material in a sample, which can solve the problems found in the above described prior art methods.

According to the present invention, there is provided a composition for detecting or quantitatively measuring a peroxide active material in a sample, comprising an organic hydroperoxide, a chromogen, and an iron (Ill) complex of the formula:

$$[(OOC-X-COO)_3Fe]M_3 \qquad (I)$$

wherein X is an alkylene group: $-(CH_2)_n-$ in which n is an integer of 0 to 5 or an allyl group, and M is a monovalent cation.

DETAILED DESCRIPTION OF THE INVENTION

It is known that copper (II) and iron (III)ions oxidize ascorbic acid by their oxidizing ability to generate dehydroascorbic acid. Since the copper (II) ion has a lower oxidation reaction rate than the iron (Ill) ion, the ability of copper (II) ion to eliminate the interference of ascorbic acid is weaker than that of iron (III) ion. It may be contemplated to use an iron (III) ion compound for the elimination of interference of ascorbic acid in the assay of components in the body fluids.

Many iron (Ill) ion compounds are known. When a conventional water-soluble iron (III) ion compound such as iron chloride is used, the iron (III) ion quickly reacts with water molecule present in an aqueous sample even at low pH to form an aquoiron (III) complex. Since the aquoiron (III) complex has a very high oxidation-reduction potential of 0.77 V, it reacts with an oxidation-reduction indicator which is used in the assay of body fluid components to provide the false-positive result. Therefore, such simple iron (III) ion compound is not preferable.

Surprisingly, the iron (III) complex of the formula (I) does not provide the false-positive result and eliminate the influence of reducing agents including ascorbic acid, when it is added to the assay reagent for the body fluid components.

In the formula (I), M represents a monovalent cation, and preferred examples of the monovalent cation are ammonium ion, monoalkylammonium ion, dialkylammonium ion, trialkylammonium ion, tetraalkylammonium ion, pyridinium ion, pyrrolium ion, anilium ion, hydrazinium ion, and the like. The alkyl is preferably a lower alkyl, in particular, methyl or ethyl.

In the alkylene group: $-(CH_2)_n-$, n is usually an integer of 0 to 5, preferably 0 to 3, more preferably 0.

Preferred examples of the iron (III) complex is ammonium iron (III) oxalate. In a case of ammonium iron (III) oxalate, it is contained in a concentration of at least 1 mmol/liter, preferably from 20 to 100 mmol/liter in an impregnation liquid to be used in the preparation of test paper piece.

A solution containing the composition of the present invention is preferably impregnated in a porous carrier such as a paper sheet and dried, and a small piece of the impregnated carrier is supported on a supporting member such as a plastic stick.

pH of the assay system is usually from 3 to 8, preferably from 5 to 7.

Herein, the peroxide active material is used in a conventional meaning, and includes hydrogen peroxide, organic hydroperoxides, radicals generated therefrom, and active oxygen.

The organic hydroperoxide and the chromogen are also well known in the art.

Preferred examples of the organic hydroperoxide are cumene hydroperoxide, 2,5-dimethyl-2,5-bis(hydroperoxy)hexane, p-menthane hydroperoxide, acetylcyclohexylsulfonyl peroxide, and the like.

Preferred examples of the chromogen are o-tolidine, 3,3',5,5'-tetramethylbenzidine, combinations of Trinder's reagents (e.g., phenol, N-ethyl-N-(2-hydroxy-3-sulfopropyl)aniline, N-sulfo propylaniline, etc.)and couplers (e.g., 4-aminoantipyrine, etc.), and the like.

Examples of the samples which contain the peroxide active materials are body fluids such as urine, blood, saliva, perspiration, ascites, tear drops and feces, and other liquid samples such as fruit juice, vegetable soup, etc.

EXAMPLES

The present invention will be explained further in detail by the following Examples.

EXAMPLE 1

Preparation of a testing piece for detecting occult blood in urine (1) Testing piece A Whatman filter paper (3 mmChr; 20×20 cm) was impregnated with the Solution 1 having the following composition and dried at 80° C. for 30 minutes. Further, the filter paper was impregnated with the Solution 2 having the following composition and dried at 50° C. for 15 minutes.

| Solution 1: containing 26 mmol/liter of ammonium iron (III) oxalate | |
| --- | --- |
| 3M Tris-malonic acid buffer (pH 6.5) | 36.6 ml |
| Sodium laurylsulfate | 300 mg |
| Cumene hydroperoxide | 4 ml |
| Ammonium iron (III) oxalate trihydrate | 1.12 g |
| Purified water | 9.4 ml |
| Ethanol | 50 ml |
| (Total | 100 ml) |
| Solution 2 | |
| 3,3',5,5'-Tetramethylbenzidene | 2 g |
| 6-Methoxyquinoline | 1 ml |
| 20% PVP (K-30) ethanol solution | 30 ml |
| Toluene | 69 ml |
| (Total | 100 ml) |

The impregnated filter paper was cut to a piece of 5 mm ×5 mm and adhered on an end of a polyethylene terephthalate sheet having sizes of 5 mm×50 mm with a double-sided adhesive tape to obtain a testing piece carrying a testing paper part.

(2) Sample

In urine, bovine blood hemoglobin and optionally ascorbic acid were added and dissolved to prepare a sample urine solution.

(3) Measurement

The testing piece was immersed in the sample urine solution and reacted for a determined time (one minute) and then a reflectance at a wavelength of 640 nm from the testing paper was measured using a color difference meter SZΣ 80 (manufactured by Nippon Denshoku Kogyo Co., Ltd.).

The results are shown in Table 1.

TABLE 1

| Urine test sample | | Reflectance (%) on testing paper | |
| --- | --- | --- | --- |
| Content of hemoglobin (mg/dl) | Content of ascorbic acid (mg/dl) | Without ammonium iron (III) oxalate | With ammonium iron (III) oxalate |
| 0 | 0 | 87.52 | 88.23 |
| 0.08 | 0 | 29.58 | 29.51 |
| 0.08 | 20 | 71.60 | 30.95 |
| 0.08 | 50 | 79.40 | 56.65 |

With or without ammonium iron (III) oxalate, the both testing pieces were well colored blue by the sample urine solution containing 0.08 mg/dl of bovine blood hemoglobin in the absence of ascorbic acid.

When 20 mg/dl of ascorbic acid was added, the testing piece containing no ammonium iron (III) oxalate was not well colored blue. On the other hand, the testing piece containing ammonium iron (III) oxalate according to the present invention was not influenced by ascorbic acid, and well colored blue even at the ascorbic acid content of 50 mg/dl.

EXAMPLE 2

Preparation of a testing piece for detecting occult blood

The following Solution A was coated on an opaque polyethylene terephthalate film at a wet thickness of 200 μm and dried at 50° C. for 15 minutes.

| Solution A | |
| --- | --- |
| 3,3',5,5'-Tetramethylbenzidene | 2 g |
| 6-Methoxyquinoline | 1 ml |

| -continued | |
|---|---|
| 20% PVP (K-90) ethanol solution | 30 ml |
| Toluene | 69 ml |
| (Total | 100 ml) |

With the following Solution B, a cotton woven fabric or a woven fabric of mixed polyester-nylon yarn was impregnated and dried at 50° C. for 30 minutes.

| Solution B: containing 26 mmol/liter of ammonium iron (III) oxalate | |
|---|---|
| 3M Tris-malonic acid buffer (pH 6.5) | 36.6 ml |
| Sodium laurylsulfate | 300 mg |
| Cumene hydroperoxide | 4 ml |
| Ammonium iron (III) oxalate trihydrate | 1.12 g |
| Purified water | 9.4 ml |
| Ethanol | 50 ml |
| (Total | 100 ml) |

The fabric containing the reagent was wet with a 0.01% aqueous solution of Triton X-100 and pressed over the reagent layer formed on the polyethylene terephthalate film.

The laminate was cut to a size of 5 mm×7 mm and adhered on an end of an opaque polyethylene terephthalate film having a size of 5 mm×80 mm with a double-sided adhesive tape.

Samples

In a purified water containing 0.08 mg/dl of bovine blood hemoglobin, ascorbic acid was dissolved in a concentration of 0, 5, 10 and 20 mg/l to prepare the samples.

Measurement

On the reagent laminate of the testing piece, 6 pm of each sample was spotted and incubated at 37° C. After 5 to 7 minutes from the start of incubation, a reflectance on the surface of reagent laminate was monitored. With the reflectance from the reagent laminate spotted by the sample containing no ascorbic acid being 1 (one), the relative reflectance of the laminate spotted by each sample was measured. The relative reflectance was between 1.00 and 1.05.

From the above results, it is understood that the influence of ascorbic acid was suppressed at any concentration of ascorbic acid.

What is claimed is:

1. A composition for detecting or quantitatively measuring a peroxide active material in a sample, comprising an organic hydroperoxide, a chromogen, a buffer for maintaining the pH range of 5 to 7, and an iron (III) complex of the formula:

$$((OOC-X-COO)_3Fe)M_3 \qquad (I)$$

wherein X is an alkylene group represented by the formula $-(CH_2)_n-$ in which n is an integer of 0 to 5, and M is a monovalent cation selected from the group consisting of ammonium ion, monoalkylammonium ion, dialkylammonium ion, trialkylammonium ion, tetraalkylammonium ion, pyridinium ion, pyrrolium ion, anilium ion and hydrazinium ion.

2. The composition according to claim 1, wherein said monovalent cation is an ammonium ion.

3. The composition according to claim 1, wherein said iron (III) complex is ammonium iron (III) oxalate.

4. The composition according to claim 1, wherein n is an integer of 0 to 3.

5. The composition according to claim 1, wherein said iron (III) complex is ammonium iron (III) oxalate present in a concentration of at least 1 mmol/liter.

6. The composition according to claim 1, wherein said organic hydroperoxide is selected from the group consisting of cumene hydroperoxide, 2,5-dimethyl-2,5-bis(hydroperoxy)hexane, p-menthane hydroperoxide and acetylcyclohexylsulfonyl peroxide.

7. The composition according to claim 1, wherein said chromogen is selected from the group consisting of o-tolidine, 3,3',5,5'-tetramethylbenzidine, phenol, N-ethyl-N-(2-hydroxy-3-sulfopropyl)aniline, N-sulfopropylaniline, and 4-aminoantipyrine.

* * * * *